United States Patent
Edlauer et al.

(10) Patent No.: US 8,218,843 B2
(45) Date of Patent: Jul. 10, 2012

(54) METHOD FOR REGISTERING TWO-DIMENSIONAL IMAGE DATA, COMPUTER PROGRAM PRODUCT, NAVIGATION METHOD FOR NAVIGATING A TREATMENT APPARATUS IN THE MEDICAL FIELD, AND COMPUTATIONAL DEVICE FOR REGISTERING TWO-DIMENSIONAL IMAGE DATA

(75) Inventors: Martin Edlauer, München (DE); Uli Mezger, München (DE); Robert Essenreiter, München (DE); Manfred Weiser, München (DE)

(73) Assignee: BrainLAB AG, Feldkirchen (DE)

( * ) Notice: Subject to any disclaimer, the term of this patent is extended or adjusted under 35 U.S.C. 154(b) by 949 days.

(21) Appl. No.: 12/243,148

(22) Filed: Oct. 1, 2008

(65) Prior Publication Data

US 2009/0087063 A1 Apr. 2, 2009

Related U.S. Application Data

(60) Provisional application No. 60/979,521, filed on Oct. 12, 2007.

(30) Foreign Application Priority Data

Oct. 1, 2007 (EP) .................................... 07117633

(51) Int. Cl.
*G06K 9/60* (2006.01)
*G06T 15/00* (2011.01)
*G06T 19/00* (2011.01)
*G01N 23/083* (2006.01)

(52) U.S. Cl. ........ 382/131; 382/154; 382/294; 378/210; 378/901

(58) Field of Classification Search .................. 382/128, 382/131, 132, 154, 276, 293–298, 325; 378/162, 378/204, 205, 210, 901; 600/427
See application file for complete search history.

(56) References Cited

U.S. PATENT DOCUMENTS

| 4,791,934 A | 12/1988 | Brunnett | |
|---|---|---|---|
| 5,951,475 A * | 9/1999 | Gueziec et al. | 600/425 |
| 2005/0004454 A1 * | 1/2005 | Mitschke et al. | 600/427 |
| 2005/0271302 A1 * | 12/2005 | Khamene et al. | 382/294 |

FOREIGN PATENT DOCUMENTS

DE 103 22 738 12/2004

OTHER PUBLICATIONS

Clippe et al., "Patient Setup Error Measurement Using 3D Intensity-Based Image Registration Techniques", International Journal of Radiation Oncology, vol. 56, No. 1, 2003, pp. 259-265.

(Continued)

*Primary Examiner* — Anastasia Midkiff
(74) *Attorney, Agent, or Firm* — Renner, Otto, Boisselle & Sklar, LLP

(57) ABSTRACT

The present application relates to a method for registering two-dimensional image data, comprising the steps of:
  providing a registered three-dimensional image data set of an object under examination;
  providing a two-dimensional image data set of the object under examination which is to be registered;
  generating synthetic two-dimensional image data sets of the object under examination from the three-dimensional image data set, wherein the synthetic two-dimensional image data sets to be generated are parameterized with regard to parameters which describe the two-dimensional image data set to be registered;
  comparing the parameterized synthetic two-dimensional image data sets with the two-dimensional image data set to be registered, and finding the parameterized synthetic two-dimensional image data set having the greatest similarity to the two-dimensional image data set to be registered;
  on the basis of this, ascertaining the spatial relationship between the two-dimensional image data set to be registered and the registered three-dimensional image data set, and thus registering the two-dimensional image data set.

12 Claims, 1 Drawing Sheet

OTHER PUBLICATIONS

Penney et al., "Validation of a two-to three-dimensional registration algorithm for aligning preoperative CT images and intraoperative fluoroscopy images", Medical Physics, AIP, vol. 28, No. 6, 2001, pp. 1024-1032.

Zöllei, L., "2D-3D Rigid-Body Registration of X-Ray Fluoroscopy and CT Images", Thesis At Masachusetts Institute of Technology, 2001, pp. 1-113.

* cited by examiner

METHOD FOR REGISTERING TWO-DIMENSIONAL IMAGE DATA, COMPUTER PROGRAM PRODUCT, NAVIGATION METHOD FOR NAVIGATING A TREATMENT APPARATUS IN THE MEDICAL FIELD, AND COMPUTATIONAL DEVICE FOR REGISTERING TWO-DIMENSIONAL IMAGE DATA

RELATED APPLICATION DATA

This application claims priority of U.S. Provisional Application No. 60/979,521 filed on Oct. 12, 2007, which is incorporated herein by reference in its entirety.

FIELD OF THE INVENTION

The invention relates to a method for registering two-dimensional image data, a computer program product comprising a program code for performing the method, a navigation method for navigating a treatment apparatus in the medical field which is based on the method in accordance with the invention for registering two-dimensional image data, and a computational device for registering two-dimensional image data.

PRIOR ART

Various methods for registering image data are already known from the prior art. The following definition with regard to registration is to be used in the following: the n-dimensional image of a body is registered when an image data point has been assigned to every spatial position of the mapped points, wherein these can be absolute or relative positional specifications; the choice of coordinate system is arbitrary and/or adapted to the problem. Cartesian coordinates, spherical coordinates or cylindrical coordinates can for example be used.

The whole purpose of registered image data is, in the vast majority of cases, the use of the registered image data sets in navigation-assisted operations in the medical field. Surgical incisions, which require a high level of precision, can be precisely planned beforehand and subsequently performed with image assistance. To this end, a treatment apparatus to be navigated, such as for example a scalpel, is generally provided with a so-called marker device. This marker device on the treatment apparatus to be navigated is detected by a camera system at the same time as another marker device which is spatially situated at a known position. The relative position between the marker device on the treatment apparatus to be navigated on the one hand and the second marker device on the other hand is ascertained, from which the position of the treatment apparatus to be navigated is deduced. On a screen unit, which the surgeon has in view during the operation, a registered image data set is then displayed in which the current position of the treatment apparatus to be navigated is simultaneously displayed. This type of display presumes that spatial positions have also been assigned to the image data points; navigation on the basis of a non-registered image data set is not possible.

There are many different image data sets, on the basis of which it is possible to navigate. For instance, it is in principle possible to navigate on the basis of registered two-dimensional image data sets (for example, on the basis of conventional x-ray recordings). It is also possible to navigate on the basis of registered three-dimensional image data sets such as are for example generated in computer tomography or nuclear magnetic resonance recordings (MRT). In the case of three-dimensional image data sets, sectional representations through various planes are often displayed to the surgeon on a screen.

Now, it is occasionally the case that variously dimensional image data sets of a body are available but that not all the image data sets are registered. Specifically, so-called "CT-fluoroscopic matching" is known from the prior art (U.S. Pat. No. 4,791,934 by Brunnett), wherein the surgeon is provided with a non-registered three-dimensional image data set, such as for example a CT recording. In the operating theatre, a two-dimensional image data set is generated in which the spatial position of the patient in a defined coordinate system is known, i.e. a registered two-dimensional recording is produced, as for example in a conventional fluoroscopic image. The patent specification then teaches how the registered two-dimensional image data sets are matched to the non-registered three-dimensional data sets, a correspondence is generated between the images. To this end, synthetic two-dimensional images are generated from the three-dimensional image data, wherein these can be so-called digitally reconstructed radiograms (DRRs) or sectional images ("slice cuts"). The artificially generated two-dimensional images are then compared with the registered actual two-dimensional image data set. The comparison is made using a measurement of similarity; for example, mutually correlated information is respectively compared. Other ways exist and have since become known from the prior art. Starting from a given parameterization of the image synthesis process, a set of parameters z is iteratively changed until a configuration is found which provides the greatest similarity between the synthetic two-dimensional image and the actually recorded two-dimensional image which is registered. The spatial positions of the image data points in the three-dimensional image data set are then deduced from the known spatial position of the image data points in the registered two-dimensional image data set, and it is then possible to register the three-dimensional image data set. Navigation can then be performed on the basis of the registered three-dimensional image data set.

DE 103 22 738 A1 is also known from the prior art and discloses a method for the marker-free automatic fusion of two-dimensional fluoroscopic C-arc images with pre-operative three-dimensional images using an intra-operatively acquired three-dimensional data set. As also in the aforementioned example of the US patent by Brunnett, a two-dimensional image data set which is registered is assumed here. On the basis of the conventionally registered two-dimensional image data sets, spatial positions of data in three-dimensional image data sets are deduced, on the basis of which an operation is on the one hand planned and on the other hand performed. However, the cited method requires an additional three-dimensional recording in addition to a pre-operatively acquired three-dimensional image data set. The pre-operatively acquired three-dimensional image data set can be generated using any recording apparatus. However, it is necessary to generate the additionally required, intra-operative three-dimensional image data set using the same recording apparatus as the one with which the registered two-dimensional image is also generated, wherein in accordance with the published patent specification, this is respectively a C-arc using which x-ray recordings can be taken. It is not possible to use DE 103 22 738 A1 for other imaging apparatuses in the medical field.

It is an object of the invention to provide an alternative method for registering two-dimensional image data, on the basis of which a navigation-assisted operating method can be performed in the medical field.

DESCRIPTION OF THE INVENTION

The method in accordance with the invention for registering two-dimensional image data enables non-registered two-dimensional image data sets which are already available to be used for navigation purposes, once they have been subjected to the method in accordance with the invention for registering. For in practice, it is often the case that two-dimensional image data sets of an object under examination are already available, and thanks to the method in accordance with the invention, it is not necessary to take another recording in order to obtain a registered two-dimensional image data set, which reduces the radiation burden on a patient, for example in the case of x-ray recordings, and reduces treatment times as a whole. In accordance with the invention, it is completely sufficient if one registered three-dimensional image data set of the object under examination is available.

In accordance with the invention, it is for example advantageously possible to retroactively register a conventional fluoroscopic recording which has been recorded by means of a C-arc. This merely requires a registered three-dimensional recording by means of a computer tomograph. Once the fluoroscopic two-dimensional recording has then been registered, it is possible—with the aid of the method in accordance with the invention—to also deduce recording parameters and to characterize the recording apparatus.

It is also possible to retroactively register two-dimensional topograms and use them for navigation purposes. In most cases, these two-dimensional topograms are generated by means of a computer tomograph prior to a complete three-dimensional recording, in order to define the recording range. To this end, an x-ray source emits fan-shaped detection rays, i.e. substantially a plane and not a three-dimensional space is irradiated, and one line of a two-dimensional image data set is generated for each image by the fanned ray. By shifting the object of the recording relative to the x-ray source, for example by passing a patient under the x-ray source, a number of recordings from different positions are generated which are then combined to form a two-dimensional recording. The two-dimensional topograms thus acquired often have a very high image quality, and it would be desirable to navigate on the basis of these recordings.

A method in accordance with the invention for registering two-dimensional image data initially comprises the steps of providing a registered three-dimensional image data set of an object under examination and providing a two-dimensional image data set of the object under examination which is to be registered, wherein it is possible to provide a three-dimensional image data set of an object under examination which is already available; alternatively, it is also possible to first generate and subsequently provide the three-dimensional image data set. The same applies to the two-dimensional image data set which is to be registered.

The image data sets can be many different image data sets. They can for example be x-ray image data sets or image data sets which have been generated by nuclear magnetic resonance recordings. Ultrasound recordings and other recording methods are also conceivable.

The object under examination is normally a patient or parts of a patient such as limbs, internal organs or a torso.

In a subsequent method step, synthetic two-dimensional image data sets of the object under examination are generated from the three-dimensional image data set. Unlike the known method of CT-fluoroscopic matching, the synthetic two-dimensional image data sets to be generated are parameterized in accordance with the invention with regard to parameters which describe the two-dimensional image data set to be registered (in CT-fluoroscopic matching, parameterization was performed in relation to the positioning of the three-dimensional image data set). The parameterization performed serves to take into account different recording situations and a configuration of the imaging apparatus when the synthetic two-dimensional image data sets were generated, which could have applied when the two-dimensional image data set to be registered was recorded. In most cases, the exact recording parameters for the non-registered two-dimensional image data set are not known beforehand.

The parameters by means of which parameterization is performed include for example spatial parameters such as three parameters of translation and/or three parameters of rotation. Using these spatial transformation parameters, it is possible to spatially describe the position of the two-dimensional recording to be registered. For an x-ray image, for instance, these parameters describe the position and orientation of the virtual camera (of the centre of projection), wherein the calculated position relates to the coordinate system in which the landmarks used for the calculation or the like are given, i.e. initially relates to an internal system of the three-dimensional data set.

In addition to the parameters described above, which describe the spatial position, it is advantageously possible to perform parameterization using one or more of the following parameters: focal length, scaling, position of the centre of the image. The focal length describes the distance between the radiation source and the image plane of the two-dimensional image data set to be registered, wherein a central ray or main axis ray is considered. The focal length is specified with respect to this ray. Scaling the two-dimensional image data set is understood to mean enlarging or reducing the image. In the case of Cartesian coordinates, the scaling is advantageously the same in both dimensions of the two-dimensional image data set, but can also be different. The same applies to two-dimensional images based on other forms of coordinate systems. The position of the centre of the image describes the location in the two-dimensional image data set to be registered at which the central mapping ray or main axis ray is mapped.

In accordance with a preferred embodiment of the invention, it is also possible to input a parameter (i.e. at least one parameter) which describes the two-dimensional image data set to be registered, wherein said parameter can be one of the parameters cited above (spatial transformation parameters or additional parameters). It can also be another parameter which allows the recording conditions when the two-dimensional image data set to be registered was created to be characterized in some way.

In accordance with the invention, the parameterized synthetic two-dimensional image data sets are compared with the two-dimensional image data set to be registered, and the parameterized synthetic two-dimensional image data set having the greatest similarity to the two-dimensional image data set to be registered is found, wherein the mathematical methods of image matching which are known in their own right are used. Finding and comparing are preferably performed using iterative methods. This can for example be based on a theory of optimization.

Once the parameterized synthetic two-dimensional image which exhibits the greatest similarity to the two-dimensional image data set to be registered has been ascertained, then the parameters which describe the two-dimensional image data set to be registered are also known, i.e. the parameters which best reflect and/or characterize the recording situation when the originally non-registered two-dimensional image data set was created. In accordance with a preferred embodiment, at least one of the ascertained parameters is output. This can be achieved by displaying the parameter or parameters, for example on a screen. It is also possible to print out the ascertained parameters by means of a printer unit.

The method in accordance with the invention for registering two-dimensional image data sets thus enables recording situations and recording apparatuses which have not previously been characterized and/or specified exactly to be characterized. The knowledge of the recording parameters acquired within the framework of the method for registering two-dimensional image data can be taken into account in future recordings using the same recording apparatus. For example, the focal length, scaling or the centre of image of the recording are then known for future recordings.

Once the parameterized synthetic two-dimensional image data set having the greatest similarity to the two-dimensional image data set to be registered has then been found, the spatial relationship between the two-dimensional image data set to be registered and the three-dimensional image data set which has already been registered is ascertained on the basis of this. Points in the three-dimensional image data set can be assigned to points in the two-dimensional image data set, and the two-dimensional image data set is thus also then registered. Since the positions of points to be mapped—displayed in the three-dimensional image data set which is registered—are known, the positions in the synthetic parameterized two-dimensional image data set are also known. This knowledge can then be applied to the two-dimensional image data set to be registered.

Advantageously, a single mapping is ascertained which, applied to all the data points of the two-dimensional image data set to be registered, then describes the spatial position of the points to be mapped. It is however also possible to specify a sequence of mappings which, sequentially applied to all the data points of the two-dimensional image data set to be registered, then describe the spatial position of the points to be mapped.

In accordance with a preferred embodiment of the invention, an image-generating method is simulated which uses a conical or fanned ray as a detection ray, in order to generate the synthetic two-dimensional image data sets, wherein the geometric relationships, in particular projections, which occur in an actual conical or fanned ray recording are simulated, wherein values of data points along the respective individual beam direction, i.e. in the respective projection direction, are for example summed in the simulation, wherein a conical ray in the sense of the invention is characterized by a spatial aperture angle, and the conical ray irradiates a three-dimensional spatial portion. By contrast, a fanned ray in accordance with the invention is characterized by a plane fanning angle, and the ray substantially irradiates an area. While the conical ray already provides one two-dimensional image for each recording by means of a conical ray, a two-dimensional image data set recorded by means of fanned rays is first compiled from a number of individual recordings of the fanned ray. A fanned ray is thus a ray which exhibits a significant expansion in one direction, and is highly focused and/or exhibits only an exceedingly small, negligible expansion in the direction orthogonal to this.

In accordance with a preferred embodiment of the invention, the two-dimensional image data set to be registered is a fluoroscopic recording which has been recorded by means of a C-arc, wherein a conical ray is simulated as a detection ray in order to generate the synthetic two-dimensional image data sets.

In accordance with another preferred embodiment of the invention, the two-dimensional image data set to be registered is a two-dimensional topogram which has been recorded by a CT scanner, wherein a fanned ray is simulated as a detection ray in order to generate the synthetic two-dimensional image data sets. With regard to the two-dimensional topograms cited, reference is made to the above statements with respect to this type of recording.

In accordance with another aspect of the invention, the invention relates to a computer program product comprising a program code for performing the described method in accordance with the invention for registering two-dimensional image data. This computer program product can for example be a CD-ROM or DVD; it is also possible to store the program code on a memory stick. Other storage media are conceivable. The program code can be written in any programming language. It is for example possible to write a program code in C or C++ or also in a scripting language.

In accordance with another aspect of the invention, the invention relates to a navigation method for navigating a treatment apparatus in the medical field. As already described above, navigation methods are known in their own right. The claimed navigation method then comprises the following steps: registering a two-dimensional image data set in accordance with the method described above for registering two-dimensional image data; visually displaying a position of a treatment apparatus to be navigated, in the registered two-dimensional image data set; and positioning the treatment apparatus to be navigated with the aid of the visual display. The core of the claimed navigation method is thus formed by the registered two-dimensional image data set acquired in accordance with the invention. This registered two-dimensional image data set is visually displayed during an operation, and the position of the treatment apparatus to be navigated, such as for example a scalpel, is also displayed in the registered two-dimensional image data set. To this end, the entire image data set or only sections of it can be displayed. Simultaneously displaying the navigated treatment apparatus and the registered two-dimensional image data set then assists the surgeon in positioning the treatment apparatus to be navigated.

In accordance with another aspect of the invention, the invention relates to a computational device for registering two-dimensional image data. This computational device can on the one hand be a computer; on the other hand, it is also possible for it to be a CPU which is integrated into another device. The computational device comprises an input unit and a processing unit. The input unit is configured to provide a registered three-dimensional image data set of an object under examination and to provide a two-dimensional image data set of the object under examination which is to be registered, wherein the unit can refer to previously stored three-dimensional image data sets and two-dimensional image data sets. It is however also possible for these data sets to first be input into the input unit, for example relayed to it, for example as stored data sets on a data medium. It is also conceivable for them to be relayed via networks.

The processing unit is configured to generate synthetic two-dimensional image data sets of the object under examination from the three-dimensional image data set, wherein the synthetic two-dimensional image data sets to be generated are parameterized with regard to parameters which describe the two-dimensional image data set to be registered. The processing unit is also configured to compare the parameterized synthetic two-dimensional image data sets with the two-dimensional image data set to be registered and to find the parameterized synthetic two-dimensional image data set having the greatest similarity to the two-dimensional image data set to be registered. Lastly, the processing unit is configured to ascertain the spatial relationship between the two-dimensional image data set to be registered and the registered three-dimensional image data set on the basis of this, and to thus register the two-dimensional image data set. With regard to the details regarding the processing unit and with regard to the preferred embodiments regarding the processing unit, reference is made to the description of the method in accordance with the invention for registering two-dimensional image data, wherein the statements made therein also apply in their entirety to the computational device in accordance with the invention and/or the processing unit described in this paragraph.

The present invention may be even better understood by consulting the enclosed FIG. 1, which shows:

Figure 1:
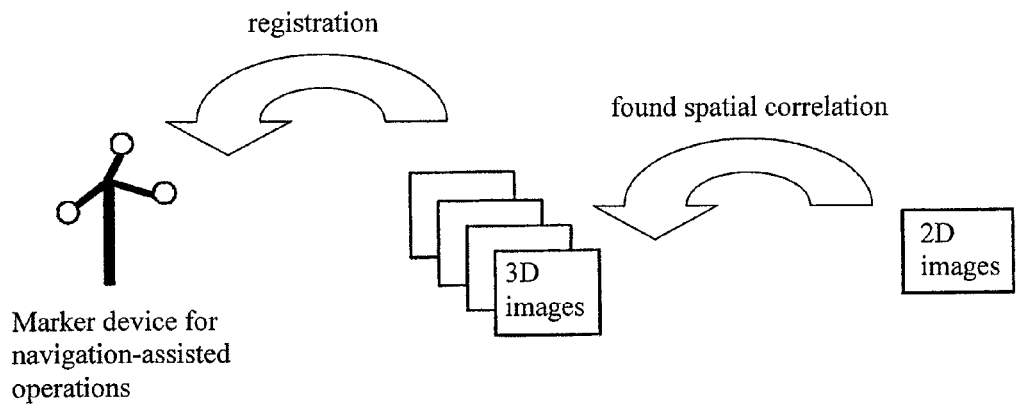
FIG. 1 illustrates matching and/or assigning a two-dimensional image data set to a three-dimensional image data set, in order to enable the two-dimensional image data set to be used for navigation-assisted operations.
Figure 2:
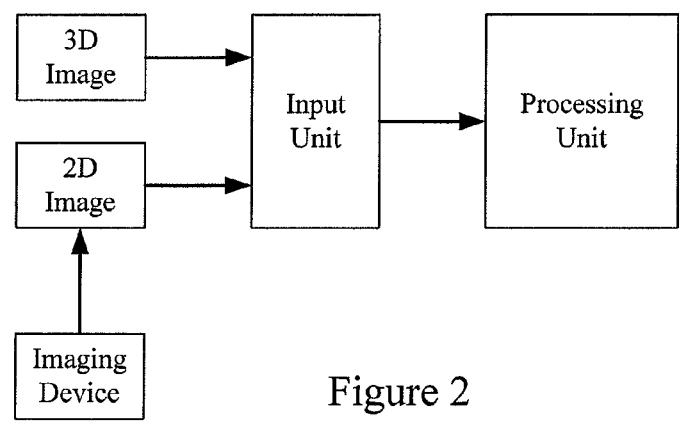
FIG. 2 is an exemplary block diagram of a computational device that may be used to implement the method according to the present invention.

A three-dimensional image data set is shown in the centre of FIG. 1. This three-dimensional image data set is usually composed of a number of sectional recordings, as is intended to be illustrated by the sequentially arranged individual images.

The three-dimensional image data set is a registered three-dimensional image data set. Each time the three-dimensional image data set was recorded, a marker device—shown on the left in the image—was mapped along with it, wherein the spatial position of the marker device and/or of the individual points which the markers represent is known. The individual markers of the marker device can be active or passive markers which either emit radiation of a particular type themselves, which is detected by a suitable receiver, or the markers can reflect radiation emitted by a radiation source (not shown); the reflected radiation is again detected by a suitable detector. The position of the marker device is ascertained on the basis of the detected radiation. Usually, the markers are for example passive markers which reflect infrared radiation.

Since the position of the marker device is known for each individual sectional recording which contributes to the three-dimensional image data set, it is known for each of the sectional recordings how the points at which the markers are situated are small spatially shown in the respective component parts of the three-dimensional image data set. In this way, a registered three-dimensional image data set is thus obtained.

A spatial correlation between the three-dimensional image data set and the two-dimensional image data set is then found using the method in accordance with the invention for registering two-dimensional image data. The spatial correlation can for example be described by one or more mapping functions. If, however, the spatial correlation between the three-dimensional image data set and the two-dimensional image data set is then known, it is possible to deduce from this the spatial position of the points mapped in the two-dimensional image data set. In this way, a registered two-dimensional image is thus obtained, and/or the two-dimensional image data set is a registered two-dimensional image data set after the method in accordance with the invention has been applied.

The invention claimed is:

1. A method for registering two-dimensional image data, comprising:
   providing a three-dimensional image data set of an object under examination, said three-dimensional image data set registered to the object;
   providing a two-dimensional image data set of the object under examination which is to be registered;
   generating, using a processor, a plurality of synthetic two-dimensional image data sets of the object under examination from the three-dimensional image data set, wherein each of the generated synthetic two-dimensional image data sets is parameterized with regard to parameters corresponding to recording conditions of a virtual image capture device;
   comparing, using a processor, each of the plurality of parameterized synthetic two-dimensional image data sets with the two-dimensional image data set, and finding a parameterized synthetic two-dimensional image data set of the plurality of parameterized two-dimensional image data sets having the greatest similarity to the two-dimensional image data set;
   based on the synthetic two-dimensional image data set having the greatest similarity with the two-dimensional image data set, ascertaining the spatial relationship between the two-dimensional image data set and the registered three-dimensional image data set, thereby registering the two-dimensional image data set to the three-dimensional image data set.

2. The method in accordance with claim 1, wherein finding and comparing are performed using an iterative method.

3. The method in accordance with claim 1, wherein parameterization is performed using three parameters of translation and/or three parameters of rotation.

4. The method in accordance with claim 1, wherein parameterization is performed using at least one of focal length, scaling, or position of the center of the image.

5. The method in accordance with claim 1, further comprising inputting at least one parameter which describes the two-dimensional image data set.

6. The method in accordance with claim 1, further comprising outputting at least one of the parameters to be assigned to the parameterized synthetic two-dimensional image data set having the greatest similarity to the two-dimensional image data set.

7. The method in accordance with claim 1, wherein generating the plurality of synthetic two-dimensional image data sets comprises using an image-generating method that uses a conical or fanned ray as a detection ray to generate the plurality of synthetic two-dimensional image data sets.

8. The method in accordance with claim 7, wherein the two-dimensional image data comprises a fluoroscopic recording recorded by means of a C-arc apparatus, and wherein a conical ray is simulated as a detection ray to generate the plurality of synthetic two-dimensional image data sets.

9. The method in accordance with claim 7, wherein the two-dimensional image data set comprises a two-dimensional topogram recorded by a CT scanner, and wherein a fanned ray is simulated as a detection ray to generate the plurality of synthetic two-dimensional image data sets.

10. A non-transitory computer readable medium comprising computer executable instructions adapted to perform the method in accordance with claim 1.

11. A navigation method for navigating a treatment apparatus in the medical field, comprising registering a two-dimensional image data set in accordance with the method in accordance with claim 1;

visually displaying a position of a treatment apparatus to be navigated, in the registered two-dimensional image data set;

positioning the treatment apparatus to be navigated with the aid of the visual display.

12. A computational device for registering two-dimensional image data, comprising:

an input unit configured to:

receive a three-dimensional image data set of an object under examination, the three-dimensional image data set registered to the object; and receive a two-dimensional image data set of the object, the two-dimensional image data set to be registered to the object;

and a processing unit configured to:

generate a plurality of synthetic two-dimensional image data sets of the object from the three-dimensional image data set, wherein each of the generated synthetic two-dimensional image data sets are parameterized with regard to parameters corresponding to recording conditions of a virtual image capture device;

compare each of the plurality of parameterized synthetic two-dimensional image data sets with the two-dimensional image data set and to find a parameterized synthetic two-dimensional image data set of the plurality of two-dimensional image data sets having the greatest similarity to the two-dimensional image data set; and based on the synthetic two-dimensional image data set having the greatest similarity with the two-dimensional image data set, ascertain the spatial relationship between the two-dimensional image data set and the registered three-dimensional image data set, and thereby registering the two-dimensional image data set to the three-dimensional image data set.

* * * * *